United States Patent
Ding et al.

(10) Patent No.: US 11,224,630 B2
(45) Date of Patent: Jan. 18, 2022

(54) MEDICINAL COMPOSITION FOR PROTECTION OF JOINTS, METHOD FOR PRODUCING THE SAME AND USE THEREOF

(71) Applicant: INFINITUS (CHINA) COMPANY LTD., Guangdong (CN)

(72) Inventors: Liugang Ding, Guangdong (CN); Zhongbao Yue, Guangdong (CN); Danlin He, Guangdong (CN); Yong Zhou, Guangdong (CN); Jian Tang, Guangdong (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 1 day.

(21) Appl. No.: 16/414,800

(22) Filed: May 17, 2019

(65) Prior Publication Data
US 2020/0206296 A1 Jul. 2, 2020

(30) Foreign Application Priority Data

Dec. 26, 2018 (CN) .......................... 201811600951.7

(51) Int. Cl.
| | | |
|---|---|---|
| *A61K 36/9066* | (2006.01) | |
| *A23L 33/105* | (2016.01) | |
| *A61P 19/02* | (2006.01) | |
| *A61K 35/32* | (2015.01) | |
| *A61K 36/488* | (2006.01) | |
| *A61K 36/8994* | (2006.01) | |

(52) U.S. Cl.
CPC ........ *A61K 36/9066* (2013.01); *A23L 33/105* (2016.08); *A61K 35/32* (2013.01); *A61K 36/488* (2013.01); *A61K 36/8994* (2013.01); *A61P 19/02* (2018.01); *A23V 2002/00* (2013.01); *A23V 2200/30* (2013.01); *A23V 2250/204* (2013.01); *A23V 2250/2112* (2013.01)

(58) Field of Classification Search
None
See application file for complete search history.

(56) References Cited

U.S. PATENT DOCUMENTS

| | | | | |
|---|---|---|---|---|
| 2004/0037903 A1* | 2/2004 | Lemmo | .................. | A61K 31/05 424/756 |
| 2014/0212519 A1* | 7/2014 | Xu | .......................... | A61K 36/90 424/738 |

FOREIGN PATENT DOCUMENTS

CN 103623006 A 3/2014

OTHER PUBLICATIONS

The 1st Office Action dated Nov. 24, 2020 regarding Chinese Patent Application No. CN201811600951.7.
Li Jiren et al., Theory of Li Jiren's arthralgia syndrome, 1st Ed., Oct. 31, 2011, Coix seed, 1-10, pp. 114-115, People's Medical Publishing House.
Tian Yan, Chinese Medicine for Intractable Diseases, 2nd edition, Henan Science and Technology Press, Jan. 31, 2018, Radix Puerariae, pp. 147-149.

\* cited by examiner

*Primary Examiner* — Terry A McKelvey
*Assistant Examiner* — Catheryne Chen
(74) *Attorney, Agent, or Firm* — Yue (Robert) Xu; Apex Attorneys at Law, LLP

(57) ABSTRACT

The present invention relates to the field of health care food technology, specifically to a traditional Chinese medicine composition with a function of protecting joints, a use thereof, a method for producing the same and a health care food thereof. The Chinese medicine composition comprises CURCUMAE LONGAE RHIZOMA extract, cartilage extract, COICIS SEMEN extract and PUERARIAE LOBATAE RADIX extract. The composition of the present disclosure has a reasonable formulation, and the ingredients cooperate with each other to achieve functions of reducing arthrocele degree, decreasing arthritis index, ameliorating biochemical index of arthritis and reducing articular cavity area through various paths and at various levels.

8 Claims, No Drawings

MEDICINAL COMPOSITION FOR PROTECTION OF JOINTS, METHOD FOR PRODUCING THE SAME AND USE THEREOF

CROSS REFERENCE TO RELATED APPLICATIONS

This application claims the priority of Chinese Patent Application No. 201811600951.7, filed on Dec. 26, 2018, and the disclosures of which are hereby incorporated by reference.

FIELD

The present disclosure relates to the field of health care food technology, specifically to a traditional Chinese medicine composition for protecting joint, a use thereof, a method for producing the same and a health care food thereof.

BACKGROUND

Osteoarthritis (OA) is a common chronic disease having characters of gradually losing articular cartilage, subchondral bone sclerosis and synovitis. Osteoarthritis of the knee is a clinical common degenerative joint disease, and the main clinical features are chronic pain of joint, swelling, stiffness at morning and even limited mobility, and joint deformity. The prevalence rate of middle-aged and elderly people is higher, women are more afflicted than men, and the incidence rate is gradually increasing with age. Osteoarthritis is a chronic, disabling disease.

Researches have shown that interleukin (IL) plays a considerable role in the pathological process of osteoarthritis of the knee, which is the main cause of articular cartilage degradation and synovial membrane inflammatory response. For example, all of IL-1, IL-6, IL-7, IL-8, IL-17 and IL-18 may accelerate the damage of cartilage. However, other cytokines such as IL-4, IL-9, IL-10 and IL-13 may play positive roles to protect the cartilage from being damaged. IL-1 and TNF-α are important inflammatory cytokines of human body, which participates in the progressive damage of cartilage in pathology of osteoarthritis, so that changes the normal structure and function of cartilage cells, facilitating the generation and development of osteoarthritis in the knee. Factors that facilitate damage of the cartilage, for example, chondrocyte apoptosis, degradation of cartilage cell matrix, synovial membrane inflammatory lesions and bone metabolism, include an internal path and an external path. The former is the degradation process of cartilage cells themselves, and the latter is the process of cartilage destruction by joint synovial fluid. And enzymatic substances degrading the extracellular matrix play an important role in both paths. Matrix metalloproteinase 3 (MMP-3) is a zinc ion-dependent enzyme, which has a main function of degrading extracellular matrix. In the early period of osteoarthritis, MMP-3 may destroy and degrade proteoglycans, and cause the losing of small molecular proteoglycans, resulting in reduced cartilage elasticity and making the arched network structure loose, so that the stress capacity of cartilage is also reduced, and proteoglycan also has a relatively weak winding protective effect on type II collagen. COL-II is the main collagen component in articular cartilage, which ensures the integrity of the articular cartilage structure.

Osteoarthritis of the knee is a category of "Bi disease" in traditional Chinese medicine. The main cause is Feng, cold, dampness and internal resistance, joint and main and collateral channels obstruction, resulting in poor circulation and dysfunction of Qi and blood. In traditional Chinese medicine, understanding and treatment of Osteoarthritis of the knee has a long history. *The Yellow Emperor's Classic of Internal Medicine* has the discussion of "the liver works on tendons, and the kidney works on bones". Kidney is the origin of congenital constitution, stores essential substances and works on bones. If deficiency of the kidney occurs, the bone marrow will be deficient, osteoporosis occurs, Qi and blood will be deficiency, tendons and bones will be dystrophic, easy to be affected by the exogenous pathogens and develops to a Bi disease in the knee. Bi disease obstacles the tendons and bones, muscles, joints, leading to poor Qi and blood circulation, and the obstacle results in pain.

At present, no one has combined cartilage extract, CURCUMAE LONGAE RHIZOMA, COICIS SEMEN and PUERARIAE LOBATAE RADIX together to make a composition for reducing arthrocele degree, decreasing arthritis index, ameliorating physiological index of arthritis and reducing articular cavity area.

SUMMARY

In view of this, the present disclosure provides a Chines medicine composition for protecting the joint, a use thereof, a method for producing the same and a health care food thereof. The traditional Chinese medicine composition has functions of synergistically reducing arthrocele degree, decreasing arthritis index, ameliorating physiological index of arthritis and reducing articular cavity area.

In order to achieve the above object of the disclosure, the present disclosure provides following technical solutions.

The present disclosure provides a traditional Chinese medicine composition with a function of protecting joints, comprising CURCUMAE LONGAE RHIZOMA extract, cartilage extract, COICIS SEMEN extract and PUERARIAE LOBATAE RADIX extract.

In the present disclosure, active ingredients such as CURCUMAE LONGAE RHIZOMA extract, cartilage extract, COICIS SEMEN extract and PUERARIAE LOBATAE RADIX extract are used to prepare the composition.

CURCUMAE LONGAE RHIZOMA may dredge the blood vessels and promote the circulation of Qi, induce menstruation to relieve menalgia, and can be used for treating thoracic tingling, amenorrhea and dysmenorrhea, rheumatism and brachialgia, abdominal mass, and swelling caused by tumble. When CURCUMAE LONGAE RHIZOMA is used in treating osteoarthritis of the knee, the effects on relieving pain and anti-inflammation are remarkable, and the safety is high and side effects are few. Therein, the component curcumin may also improve the symptoms of Osteoarthritis of the knee by affecting FLs, cytokines (TNF-α, IL-1, VEGF), metalloproteinases (MMP-1, 13), and signal pathways of NF-KB.

Cartilage extract comprises active ingredients such as collagen, chondroitin sulfate and hyaluronic acid, etc., which may inhibit the growth of abnormally proliferating blood vessels, reconstruct articular cartilage, and inhibit cartilage degradation. The combination of the two can synergistically improve the symptoms of osteoarthritis of the knee, achieving the effect of preventing Osteoarthritis of the knee. Symptoms such as joint pain, swelling, stiffness, abnormal sound, etc. are relieved.

COICIS SEMEN nourishes the spleen and removes the humidification, and the main and collateral channels are unobstructed after dehumidification. COICIS SEMEN comprises coixenolide and coixol. COICIS SEMEN has functions of analgesia and reducing the inflammatory response of body. At the same time, COICIS SEMEN may reduce the expression of VEGF-A. COICIS SEMEN effective extract obviously inhibits the expression of HIF-1α, so that inhibits the expression of MVD in synovial membrane vessels and reduce synovial membrane angiogenesis.

PUERARIAE LOBATAE RADIX has effects of expelling pathogenic factors from muscles for abatement of heat, promoting the secretion of body liquid, promoting eruption, arising yang and antidiarrheal. Puerarin contained in the PUERARIAE LOBATAE RADIX may relieve articular swelling, improve microcirculation and resist vasospasm, improving the hypercoagulability of blood vessel, so as to achieve the effect of treating arthritis.

Thus, in the present disclosure, CURCUMAE LONGAE RHIZOMA extract, cartilage extract, COICIS SEMEN extract and PUERARIAE LOBATAE RADIX extract are used to produce a composition which can synergistically reduce arthrocele degree, decrease arthritis index, ameliorate physiological index of arthritis and reduce articular cavity area through various pathways and at various levels.

Preferably, the traditional Chinese medicine composition comprises parts by weight: 1~20 parts of CURCUMAE LONGAE RHIZOMA extract, 20~40 parts of cartilage extract, 1~20 parts of COICIS SEMEN extract, and 0.1~1.0 part of PUERARIAE LOBATAE RADIX extract.

Preferably, the traditional Chinese medicine composition comprises parts by weight: 5~10 parts of CURCUMAE LONGAE RHIZOMA extract, 25~35 parts of cartilage extract, 5~15 parts of COICIS SEMEN extract, and 0.1~0.5 part of PUERARIAE LOBATAE RADIX extract.

More preferably, the traditional Chinese medicine composition comprises parts by weight: 10 parts of CURCUMAE LONGAE RHIZOMA extract, 35 parts of cartilage extract, 15 parts of COICIS SEMEN extract, and 0.5 part of PUERARIAE LOBATAE RADIX extract.

In one specific embodiment provided in the present disclosure, the traditional Chinese medicine composition comprises parts by weight: 5 parts of CURCUMAE LONGAE RHIZOMA extract, 25 parts of cartilage extract, 5 parts of COICIS SEMEN extract, and 0.1 part of PUERARIAE LOBATAE RADIX extract.

In another specific embodiment provided in the present disclosure, the traditional Chinese medicine composition comprises parts by weight: 8 parts of CURCUMAE LONGAE RHIZOMA extract, 30 parts of cartilage extract, 10 parts of COICIS SEMEN extract, and 0.3 part of PUERARIAE LOBATAE RADIX extract.

In the present disclosure, a use of the traditional Chinese medicine composition in manufacturing a health care food for relieving arthritis is also provided.

In the present disclosure, the relieving arthritis is one or more effects selected from reducing arthrocele degree, decreasing arthritis index, ameliorating physiological index of arthritis and reducing articular cavity area.

In the present disclosure, a method for producing the traditional Chinese medicine composition is also provided, comprising mixing CURCUMAE LONGAE RHIZOMA extract, cartilage extract, COICIS SEMEN extract and PUERARIAE LOBATAE RADIX extract.

In the present disclosure, a health care food comprising the traditional Chinese medicine composition is also provided. The traditional Chinese medicine composition comprises CURCUMAE LONGAE RHIZOMA extract, cartilage extract, COICIS SEMEN extract and PUERARIAE LOBATAE RADIX extract.

Preferably, the health care food further comprises a food additive.

Preferably, the dosage form of the health care food is oral liquid, capsule, tablet, powder, effervescent, granule or tableted candy.

In the present disclosure, a traditional Chinese medicine composition with a function of protecting joints, a use thereof, a method for producing the same and a health care food thereof is provided. The traditional Chinese medicine composition comprises CURCUMAE LONGAE RHIZOMA extract, cartilage extract, COICIS SEMEN extract and PUERARIAE LOBATAE RADIX extract. The present disclosure has the following technical effects.

(1) In the present disclosure, a composition for reducing arthrocele degree, decreasing arthritis index, ameliorating physiological index of arthritis and reducing articular cavity area is provided. The composition mainly comprises CURCUMAE LONGAE RHIZOMA extract, cartilage extract, COICIS SEMEN extract and PUERARIAE LOBATAE RADIX extract, and the composition is used to prepare health care foods having functions of reducing arthrocele degree, decreasing arthritis index, ameliorating physiological index of arthritis and reducing articular cavity area.

(2) In the composition of the present invention, various ingredients are rationally formulated and cooperate with each other to achieve effects of reducing arthrocele degree, decreasing arthritis index, ameliorating physiological index of arthritis and reducing articular cavity area through multiple ways and at various levels.

(3) In the present disclosure, results show that the composition of the present disclosure has functions of relieving arthrocele and lowering arthritis index, indicating that combining CURCUMAE LONGAE RHIZOMA extract, cartilage extract, COICIS SEMEN extract and PUERARIAE LOBATAE RADIX extract together has a synergistic effect.

(4) Osteoarthritis of the knee is closely related to IL-1β, IL-6 and TNF-α in the blood, PGE2 and IL-1β in the tissue, and MMP-3 and COL-II in the synovial fluid, etc. In the present disclosure, the contents of interleukin 1β, interleukin 5 and tumor necrosis factor α in the serum, matrix metalloproteinase-3 and type II collagen in the synovial fluid, prostaglandin and interleukin-1β in the swollen tissue, and articular cavity can be improved by the composition of the present disclosure. Especially, using CURCUMAE LONGAE RHIZOMA extract, cartilage extract, COICIS SEMEN extract and PUERARIAE LOBATAE RADIX extract together has a synergistic effect.

DETAILED DESCRIPTION

In the present disclosure, a traditional Chinese medicine composition for protecting joint, a use thereof, a method for producing the same and a health care food thereof is provided. One of ordinary skill in the art can learn from the contents of this document and appropriately improve the process parameters to achieve the disclosure. It is should be noted that all such alternatives and modifications are obvious to one of ordinary skill in the art and are considered to be included in the present invention. The method and application of the present disclosure have been described in terms of preferred embodiments. It will be apparent to one of ordinary skill in the art that the methods and applications described herein may be modified or modified and combined to implement and practice the techniques of the present disclosure without departing from the spirit and scope of protection of the present disclosure.

In *TCM Disease Diagnosis and Treatment Terminology-Diseases*, Osteoarthritis of the knee is specifically called "Bi in the knee". Blood stasis leads to Bi disease, and long-time Bi disease certainly leads to stagnate of blood, thus eliminating blood stasis is necessary in treating Bi disease. Traditional Chinese medicine CURCUMAE LONGAE RHIZOMA is one of the medicines for invigorating blood circulation and eliminating stasis, which is the dry rhizome of zingiberaceae *Curcuma Longa* L. or *Curcuma rcenyujin* Y, H. Chenet C. Ling. It is pungent and bitter in taste and warm in nature, works on the spleen and liver channel, having functions of dredging the blood vessels and promoting the circulation of Qi. The traditional Chinese medicine thinks that weakness of the spleen and the stomach, unbalance diet may lead to poor yield of Qi and blood, lack of muscles, and malnutrition of joints in arms and legs. If the above conditions last long, Qi and blood is depletion, bones and tendons and the blood vessels are not nourished, the nutrient qi and defensive qi camp is out of harmony, the pathogen of the Feng, cold and dampness invades and effects on the tendon and vessel, resulting in the rheumatism and Bi disease. COICIS SEMEN nourishes the spleen and removes the humidification. The effective ingredient of COICIS SEMEN, coix seed oil, has effects of anti-inflammation and relieving pain, and effectively remits the inflammatory responses. PUERARIAE LOBATAE RADIX has functions of expelling pathogenic factors from muscles for abatement of heat, promoting the secretion of body liquid, promoting eruption, arising yang and antidiarrheal. The neovascularization factor contained in cartilage inhibits the growth of abnormally proliferating blood vessels, reconstructs articular cartilage, and inhibits cartilage degradation. A combination of CURCUMAE LONGAE RHIZOMA, COICIS SEMEN, PUERARIAE LOBATAE RADIX and cartilage extract has a synergistic function of reducing arthrocele degree, decreasing arthritis index, ameliorating physiological index of arthritis and reducing articular cavity area.

In the present disclosure, a composition was obtained by mixing CURCUMAE LONGAE RHIZOMA extract, COICIS SEMEN extract, PUERARIAE LOBATAE RADIX extract and cartilage extract, all were purchased on the market or hand-made. All the raw materials or adjuvants used in the traditional Chinese medicine composition and the use thereof, the method for producing the same and the health care food thereof provided by the present disclosure were purchased from the market. CURCUMAE LONGAE RHIZOMA extract was purchased from CHR Hansen (China) Co., Ltd.; COICIS SEMEN extract was purchased from Shaanxi Jiahe Phytochem Co., Ltd; PUERARIAE LOBATAE RADIX extract was purchased from Huangshan greenxtract Biotechnology Co., Ltd., cartilage extract was purchased from Meitek Technology (Qingdao) Co., Ltd.

In the present disclosure, the cartilage extract was purchased from the market, or hand-made, and the extraction method was: pre-treatment, enzymatic hydrolysis, impurity removal, drying and the like.

The present disclosure will be further illustrated in conjunction with examples hereinafter.

Example 1

A composition for reducing arthrocele degree, decreasing arthritis index, ameliorating physiological index of arthritis and reducing articular cavity area provided by the present disclosure was made from the following active ingredients in parts by weight:

CURCUMAE LONGAE RHIZOMA extract 10 parts, cartilage extract 35 parts, COICIS SEMEN extract 15 parts, PUERARIAE LOBATAE RADIX extract 0.5 part.

The composition for reducing arthrocele degree, decreasing arthritis index, ameliorating physiological index of arthritis and reducing articular cavity area was obtained by the following method: CURCUMAE LONGAE RHIZOMA extract, cartilage extract, COICIS SEMEN extract and PUERARIAE LOBATAE RADIX extract were weighed according to the weight ratio, other adjuvants and water were added. After processes of preparation, encapsulation, sterilization, etc., an oral liquid was obtained, which could be used as a health care food or food.

Example 2

A composition for reducing arthrocele degree, decreasing arthritis index, ameliorating physiological index of arthritis and reducing articular cavity area provided by the present disclosure was made from the following active ingredients in parts by weight:

CURCUMAE LONGAE RHIZOMA extract 10 parts, cartilage extract 35 parts, COICIS SEMEN extract 15 parts, PUERARIAE LOBATAE RADIX extract 0.5 part.

The composition for reducing arthrocele degree, decreasing arthritis index, ameliorating physiological index of arthritis and reducing articular cavity area was obtained by the following method: CURCUMAE LONGAE RHIZOMA extract, cartilage extract, COICIS SEMEN extract, PUERARIAE LOBATAE RADIX extract and other adjuvants were weighed. After sieving, mixing, and packing, a composition for reducing arthrocele degree, decreasing arthritis index, ameliorating physiological index of arthritis and reducing articular cavity area was obtained. The dosage form of the composition was powder, and the powders could be used as a health care food or food.

Example 3

A composition for reducing arthrocele degree, decreasing arthritis index, ameliorating physiological index of arthritis and reducing articular cavity area provided by the present disclosure was made from the following active ingredients in parts by weight:

CURCUMAE LONGAE RHIZOMA extract 10 parts, cartilage extract 35 parts, COICIS SEMEN extract 15 parts, PUERARIAE LOBATAE RADIX extract 0.5 part.

The composition for reducing arthrocele degree, decreasing arthritis index, ameliorating physiological index of arthritis and reducing articular cavity area was obtained by the following method: CURCUMAE LONGAE RHIZOMA extract, cartilage extract, COICIS SEMEN extract, PUERARIAE LOBATAE RADIX extract and regular adjuvants were taken and subjected to mixing, tableting, etc. to obtain tablets or tableted candies. The tablets or tableted candies could be used as a health care food or food.

Example 4

A composition for reducing arthrocele degree, decreasing arthritis index, ameliorating physiological index of arthritis and reducing articular cavity area provided by the present disclosure was made from the following active ingredients in parts by weight:

CURCUMAE LONGAE RHIZOMA extract 10 parts, cartilage extract 35 parts, COICIS SEMEN extract 15 parts, PUERARIAE LOBATAE RADIX extract 0.5 part.

The composition for reducing arthrocele degree, decreasing arthritis index, ameliorating physiological index of arthritis and reducing articular cavity area was obtained by the following method: CURCUMAE LONGAE RHIZOMA extract, cartilage extract, COICIS SEMEN extract, PUERARIAE LOBATAE RADIX extract and regular adjuvants were taken and subjected to sieving, mixing, and filling to obtain the composition in a dosage form of hard capsule, which could be used as a health care food or food.

Example 5

A composition for reducing arthrocele degree, decreasing arthritis index, ameliorating physiological index of arthritis and reducing articular cavity area provided by the present disclosure was made from the following active ingredients in parts by weight:
CURCUMAE LONGAE RHIZOMA extract 10 parts, cartilage extract 35 parts, COICIS SEMEN extract 15 parts, PUERARIAE LOBATAE RADIX extract 0.5 part.

The composition for reducing arthrocele degree, decreasing arthritis index, ameliorating physiological index of arthritis and reducing articular cavity area was obtained by the following method: CURCUMAE LONGAE RHIZOMA extract, cartilage extract, COICIS SEMEN extract, PUERARIAE LOBATAE RADIX extract and regular adjuvants were taken and subjected to sieving, mixing, and filling to obtain the composition in a dosage form of soft capsule, which could be used as a health care food or food.

Example 6

A composition for reducing arthrocele degree, decreasing arthritis index, ameliorating physiological index of arthritis and reducing articular cavity area provided by the present disclosure was made from the following active ingredients in parts by weight:
CURCUMAE LONGAE RHIZOMA extract 10 parts, cartilage extract 35 parts, COICIS SEMEN extract 15 parts, PUERARIAE LOBATAE RADIX extract 0.5 part.

The composition for reducing arthrocele degree, decreasing arthritis index, ameliorating physiological index of arthritis and reducing articular cavity area was obtained by the following method: CURCUMAE LONGAE RHIZOMA extract, cartilage extract, COICIS SEMEN extract, PUERARIAE LOBATAE RADIX extract and regular adjuvants were taken and subjected to sieving, mixing, granulating, drying and packing to obtain the composition in a dosage form of granule, which could be used as a health care food or food.

Example 7

A composition for reducing arthrocele degree, decreasing arthritis index, ameliorating physiological index of arthritis and reducing articular cavity area provided by the present disclosure was made from the following active ingredients in parts by weight:
CURCUMAE LONGAE RHIZOMA extract 5 parts, cartilage extract 25 parts, COICIS SEMEN extract 5 parts, PUERARIAE LOBATAE RADIX extract 0.1 part.

The composition for reducing arthrocele degree, decreasing arthritis index, ameliorating physiological index of arthritis and reducing articular cavity area was obtained by the following method: CURCUMAE LONGAE RHIZOMA extract, cartilage extract, COICIS SEMEN extract, PUERARIAE LOBATAE RADIX extract and regular adjuvants were taken and subjected to mixing, encapsulating, sterilizing and other process to obtain the composition in a dosage form of oral liquid.

Example 8

A composition for reducing arthrocele degree, decreasing arthritis index, ameliorating physiological index of arthritis and reducing articular cavity area provided by the present disclosure was made from the following active ingredients in parts by weight:
CURCUMAE LONGAE RHIZOMA extract 8 parts, cartilage extract 30 parts, COICIS SEMEN extract 10 parts, PUERARIAE LOBATAE RADIX extract 0.3 part.

The composition for reducing arthrocele degree, decreasing arthritis index, ameliorating physiological index of arthritis and reducing articular cavity area was obtained by the following method: CURCUMAE LONGAE RHIZOMA extract, cartilage extract, COICIS SEMEN extract, PUERARIAE LOBATAE RADIX extract and regular adjuvants were taken and subjected to mixing, encapsulating, sterilizing and other process to obtain the composition in a dosage form of oral liquid.

Experimental Example

Pharmacodynamics research on composition for reducing arthrocele degree, decreasing arthritis index, ameliorating physiological index of arthritis and reducing articular cavity area 1. Test Agency Laboratory of Pharmacology and Toxicology, School of Pharmacy, Sun Yat-sen University.

2. Purpose of the Test

To study whether the health care food or food of the present disclosure has functions of reducing arthrocele degree, decreasing arthritis index, ameliorating physiological index of arthritis and reducing articular cavity area.

3. Materials

The health care food or food of the present disclosure: composition obtained in Example 2 (a formulation for relieving arthritis), provided by Infinitus (China) Co., Ltd., which was yellow powders. The recommended oral administration amount of human being was 1.56 g/day, once a day; body weight of each person was set as 60 kg, so the equivalent dose of the composition was 0.026 g/kg·bw. The daily administration amount of cartilage extract was 1 g/day; body weight of each person was set as 60 kg, so the equivalent dose was 0.0167 g/kg·bw. The daily administration amount of CURCUMAE LONGAE RHIZOMA extract was 0.2 g/day; body weight of each person was set as 60 kg, so the equivalent dose was 3.333 mg/kg·bw. The daily administration amount of COICIS SEMEN extract was 0.2 g/day; body weight of each person was set as 60 kg, so the equivalent dose was 3.333 mg/kg·bw.

4. Method (Efficacy Study in Animal)
4.1 Design of the Dosage

TABLE 1

Administration amount according to body weight

| Group | Multiples amounting to human dosage | Dosage for rat |
|---|---|---|
| Cartilage extract | 10 | 166.67 mg/kg |
| CURCUMAE LONGAE RHIZOMA extract | 10 | 33.33 mg/kg |
| COICIS SEMEN extract | 10 | 33.33 mg/kg |
| Cartilage extract + CURCUMAE LONGAE RHIZOMA extract | 10 | 166.67 mg/kg cartilage extract and 33.33 mg/kg CURCUMAE LONGAE RHIZOMA extract |
| Cartilage extract + CURCUMAE LONGAE RHIZOMA extract + COICIS SEMEN extract | 10 | 166.67 mg/kg cartilage extract, 33.33 mg/kg CURCUMAE LONGAE RHIZOMA extract and 33.33 mg/kg COICIS SEMEN extract |
| Example 2 | 10 | 0.26 g/kg |

The dosage design: administration amount of rat in the formula group was 0.26 g/kg, equal to 10 multiples of the administration amount of a 60 kg-adult, 1.56 g/day;

administration amount of rat in the cartilage extract group was 166.67 mg/kg, equal to 10 multiples of the administration amount of a 60 kg-adult, 1 g/day;

administration amount of rat in the CURCUMAE LONGAE RHIZOMA extract group was 33.33 mg/kg, equal to 10 multiples of the administration amount of a 60 kg-adult, 0.2 g/day;

administration amount of rat in the COICIS SEMEN extract group was 33.33 mg/kg, equal to 10 multiples of the administration amount of a 60 kg-adult, 0.2 g/day.

The administration amount of (cartilage extract+CURCUMAE LONGAE RHIZOMA extract) group was a combination of 166.67 mg/kg cartilage extract and 33.33 mg/kg CURCUMAE LONGAE RHIZOMA extract.

The administration amount of (cartilage extract+CURCUMAE LONGAE RHIZOMA extract+COICIS SEMEN extract) group was a combination of 166.67 mg/kg cartilage extract, 33.33 mg/kg CURCUMAE LONGAE RHIZOMA extract and 33.33 mg/kg COICIS SEMEN extract.

The samples of each dosage group were fine milled, and distilled water was added and the resultant was blended and adjusted to a constant volume suitable for gavage administration.

Grouping: SD rats, female, SPF grade, 180~220 g, were purchased from Experimental Animal Center of Sun Yat-sen University. The rats were randomly divided into 8 groups, 10 rats per group. A. normal control group, B. model group, C. cartilage extract group (166.67 mg/kg), D. CURCUMAE LONGAE RHIZOMA extract group (33.33 mg/kg), E. COICIS SEMEN extract group (33.33 mg/kg), F. cartilage extract+CURCUMAE LONGAE RHIZOMA extract group (166.67 mg/kg cartilage extract+33.33 mg/kg CURCUMAE LONGAE RHIZOMA extract), G. cartilage extract+CURCUMAE LONGAE RHIZOMA extract+COICIS SEMEN extract group (166.67 mg/kg cartilage extract+33.33 mg/kg CURCUMAE LONGAE RHIZOMA extract+33.33 mg/kg COICIS SEMEN extract), and H. formula group (0.26 g/kg).

4.2 Effects on Adjuvant-Induced Arthritis Rat Model

SD rats of each group were preventively administered for 2 weeks, once a day. 2 weeks after the administration, 0.1 mL Freund's complete adjuvant was injected to right back vola pedis of rats to induce inflammation. On the same day, all the groups were administered, and continuously administered once a day for 3 weeks. After the administration, samples were collected and the following indexes were detected.

1) Observation: mental states of rats, walking, etc., were observed every day; and the body weight was weighed every 7 d.

2) Arthritis index (AI): arthritic index was evaluated by arthritis scoring method (0~4 grades). 0 point: normal, without arthritis; 1 point: erythema and slight swelling occurred on the ankle joint; 2 points: erythema and slight swelling occurred from the ankle joint to the metatarsophalangeal joint or the palm joint; 3 points: erythema and moderate swelling occurs from the ankle joint to the metatarsophalangeal joint or palm joint; 4 points: erythema and severe swelling occurs from the ankle joint to the metatarsophalangeal joint.

3) Measure of arthrocele: the volume of vola pedis was measured by the vola pedis volume measuring instrument once before the inflammation and 3 h, 3 d, 7 d, 14 d, 21 d, 30 d after the inducing of inflammation, and the difference in volume of the vola pedis before and after was used to evaluate the arthrocele degree.

4) Measure of biochemical indicators: blood sample was collected, and serum was separated to measure the contents of IL-1β, IL-6 and TNF-α by ELISA; synovial fluid was collected to measure the expression levels of MMP-3 and COL-II; and the inflammatory swelling paw was sheared off, and levels of prostaglandin PGE2 and IL-1β were measured.

5) Measure of articular cavity: after anesthesia, the ankle joint was irradiated with an ultrasound apparatus to measure the area of articular cavity of the ankle joint.

4.3 Statistics Analysis

The test data was analyzed by GraphPad Prism 7.0 biological statistical software. The data was expressed as Mean±SD; weight, arthritis index, arthrocele degree was analyzed by one-way ANOVA combining with Dunnett's multiple comparisons; and biochemical indicators, articular cavity were analyzed by one-way analysis of variance.

5. Test Result 5.1 Observation 1 h after model establishment in rat, all the model rats showed claudication. 3 h later, the inflammatory paw swelled. 18 h later, the swelling reached the peak value. 3 d later, the swelling gradually reduced, and tended to back to normal after 14 d.

Before the administration and 1 to 14 d of the preventive administration, there was no statistical difference in body weight between each group (P>0.05); 14 d after the administration, except for the normal group, all other groups were subjected to model establishment. Comparing with the normal group, from the 21$^{th}$ day of administration (the 7$^{th}$ day of model establishment), body weight of each modeled group tended to reduce; on the 28$^{th}$ day of administration (the 14$^{th}$ day of model establishment) and the 35$^{th}$ day of administration (the 21$^{th}$ day of model establishment), the body weight of modeled group showed significantly reduced (P<0.01). Comparing with the model group, test samples have no obvious effect on weight of the rats (P>0.05). Results are shown in Table 2.

TABLE 2

Effects of the composition on weight of Freund's adjuvant-induced arthritis model rats (g, Mean ± SD)

| Group | 0 d of the administration | 7 d of the administration | 14 d of the administration | 21 d of the administration | 28 d of the administration | 35 d of the administration |
| --- | --- | --- | --- | --- | --- | --- |
| A. normal group | 207.50 ± 11.54 | 222.20 ± 7.70 | 233.70 ± 12.34 | 233.30 ± 18.34 | 252.50 ± 11.16** | 279.00 ± 16.65** |
| B. model group | 208.40 ± 12.78 | 214.20 ± 15.30 | 224.40 ± 12.94 | 227.20 ± 16.80 | 232.50 ± 15.69 | 252.40 ± 26.30 |
| C. Cartilage extract group | 206.40 ± 9.35 | 213.10 ± 11.93 | 224.80 ± 14.13 | 224.00 ± 8.47 | 232.10 ± 10.57 | 253.60 ± 17.95 |
| D. CURCUMAE LONGAE RHIZOMA extract group | 206.50 ± 9.92 | 218.60 ± 9.61 | 231.60 ± 11.23 | 226.80 ± 15.66 | 235.60 ± 15.94 | 260.50 ± 13.67 |
| E. COICIS SEMEN extract group | 208.40 ± 9.25 | 219.70 ± 11.96 | 237.80 ± 18.02 | 235.30 ± 17.63 | 238.10 ± 11.92 | 257.30 ± 11.26 |
| F. Cartilage extract + CURCUMAE LONGAE RHIZOMA extract group | 208.10 ± 10.35 | 220.00 ± 12.65 | 233.80 ± 13.10 | 233.40 ± 14.03 | 245.10 ± 12.91 | 260.10 ± 14.81 |
| G. Cartilage extract + CURCUMAE LONGAE RHIZOMA extract + COICIS SEMEN extract group | 207.70 ± 7.53 | 220.40 ± 8.69 | 230.40 ± 10.56 | 234.40 ± 7.72 | 243.60 ± 14.71 | 256.50 ± 13.07 |
| H. formula group (Example 2) | 208.00 ± 10.90 | 223.80 ± 10.45 | 231.00 ± 7.94 | 234.70 ± 9.57 | 242.00 ± 14.52 | 258.20 ± 13.23 |

Comment: comparing with the model group,
*P < 0.05; and
**P < 0.01.

Comment: comparing with the model group, *: P<0.05; and **: P<0.01.

5.2 Arthritis Index

Comparing with the normal group, AI scores of the model group increased significantly (P<0.01), wherein the score of the 3$^{th}$ day after model establishment was the highest. After 3 d, the scores gradually reduced, and tended to be stable after 14 d of model establishment. Comparing with the model group, each group improved the AI score in varying degrees. In the test drugs, effects of the cartilage extract+ CURCUMAE LONGAE RHIZOMA group, cartilage extract+CURCUMAE LONGAE RHIZOMA+COICIS SEMEN group and the formula group were the most significant (P<0.05 or P<0.01); and wherein the formula group was the optimum (reference was made to Table 3).

TABLE 3

Effects of the composition on arthritis index of Freund's adjuvant-induced arthritis model rats (g, Mean ± SD)

| Group | 3 h after model establishment | 3 d after model establishment | 7 d after model establishment | 14 d after model establishment | 21 d after model establishment |
| --- | --- | --- | --- | --- | --- |
| A. normal group | 0.00 ± 0.00** | 0.00 ± 0.00** | 0.00 ± 0.00** | 0.00 ± 0.00** | 0.00 ± 0.00** |
| B. model group | 3.30 ± 0.67 | 3.90 ± 0.32 | 3.40 ± 0.52 | 3.20 ± 0.42 | 3.10 ± 0.74 |
| C. Cartilage extract group | 3.00 ± 0.47 | 3.60 ± 0.52 | 3.10 ± 0.57 | 2.80 ± 0.42 | 2.70 ± 0.67 |
| D. CURCUMAE LONGAE RHIZOMA extract group | 3.20 ± 0.63 | 3.80 ± 0.42 | 3.20 ± 0.42 | 2.90 ± 0.57 | 2.80 ± 0.79 |
| E. COICIS SEMEN extract group | 3.10 ± 0.32 | 3.60 ± 0.70 | 3.00 ± 0.47 | 2.70 ± 0.67 | 2.60 ± 0.70 |
| F. Cartilage extract + CURCUMAE LONGAE RHIZOMA extract group | 2.80 ± 0.42 | 3.40 ± 0.70 | 2.70 ± 0.48* | 2.50 ± 0.53* | 2.50 ± 0.53 |

TABLE 3-continued

Effects of the composition on arthritis index of Freund's adjuvant-induced arthritis model rats (g, Mean ± SD)

| Group | 3 h after model establishment | 3 d after model establishment | 7 d after model establishment | 14 d after model establishment | 21 d after model establishment |
|---|---|---|---|---|---|
| G. Cartilage extract + CURCUMAE LONGAE RHIZOMA extract + COICIS SEMEN extract group | 2.70 ± 0.48 | 3.30 ± 0.48 | 2.50 ± 0.53** | 2.40 ± 0.52** | 2.40 ± 0.84* |
| H. formula group (Example 2) | 2.60 ± 0.52* | 3.00 ± 0.82** | 2.60 ± 0.70** | 2.40 ± 0.52** | 2.30 ± 0.48** |

Comment: comparing with the model group,
*P < 0.05; and
**P < 0.01

5.3 Arthrocele Degree

Comparing with the normal group, the arthrocele degree of the model groups significantly increased (P<0.01), wherein the arthrocele degree of the $3^{th}$ day after model establishment was the highest. After 3 d, the arthrocele gradually reduced, and tended to be stable after 14 d of model establishment. Comparing with the model group, test samples reduced the arthrocele degree in varying degrees, wherein the effects of cartilage extract+CURCUMAE LONGAE RHIZOMA extract group, cartilage extract+CURCUMAE LONGAE RHIZOMA extract+COICIS SEMEN extract group and the formula group showed significant difference (P<0.05 or P<0.01), and the formula group was the optimum (see Table 4).

COICIS SEMEN extract group and the formula group significantly decreased the contents of IL-1β, IL-6 and TNF-α in the serum (P<0.05 or P<0.01). Results are shown in Table 5. Biochemical indicator of swelling tissue: comparing with the normal group, contents of PGE2 and IL-1β in the swelling tissue of the model group significantly increased (P<0.01). Comparing with the model group, each test sample has effect of reducing contents of PGE2 and IL-1β in the tissue at certain degree, wherein the cartilage extract+CURCUMAE LONGAE RHIZOMA extract+COICIS SEMEN extract group and the formula group significantly decreased the content of PGE2 in the tissue (P<0.05 or P<0.01); and the formula group also reduced the content IL-1 in the tissue (see Table 6). Biochemical indi-

TABLE 4

Effects of the composition on arthrocele degree of Freund's adjuvant-induced arthritis model rats (g, Mean ± SD)

| Group | 3 h after model establishment | 3 d after model establishment | 7 d after model establishment | 14 d after model establishment | 21 d after model establishment |
|---|---|---|---|---|---|
| A. normal group | 0.03 ± 0.15** | 0.04 ± 0.16** | 0.09 ± 0.12** | 0.11 ± 0.14** | 0.13 ± 0.11** |
| B. model group | 1.36 ± 0.29 | 2.39 ± 0.56 | 2.04 ± 1.07 | 1.66 ± 0.39 | 1.61 ± 0.32 |
| C. cartilage extract group | 1.37 ± 0.25 | 2.34 ± 0.69 | 1.89 ± 0.36 | 1.59 ± 0.60 | 1.51 ± 0.25 |
| D. CURCUMAE LONGAE RHIZOMA extract group | 1.37 ± 0.29 | 2.31 ± 0.49 | 1.65 ± 0.27 | 1.44 ± 0.30 | 1.39 ± 0.33 |
| E. COICIS SEMEN extract group | 1.35 ± 0.28 | 2.28 ± 0.55 | 1.72 ± 0.33 | 1.49 ± 0.21 | 1.46 ± 0.40 |
| F. cartilage extract + CURCUMAELONGAE RHIZOMA extract group | 1.28 ± 0.23 | 2.13 ± 0.46 | 1.55 ± 0.39* | 1.32 ± 0.21 | 1.25 ± 0.25 |
| G. cartilage extract + CURCUMAE LONGAE RHIZOMA extract + COICIS SEMEN extract group | 1.26 ± 0.24 | 2.07 ± 0.44 | 1.48 ± 0.25** | 1.22 ± 0.28 | 1.19 ± 0.25 |
| H. formula group (Example 2) | 1.21 ± 0.21 | 1.95 ± 0.47 | 1.34 ± 0.29** | 1.22 ± 0.33* | 1.13 ± 0.20* |

Comment: comparing with the model group,
*P < 0.05; and
**P < 0.01

5.4 Measure of Biochemical Indicators

Biochemical indicators in serum: comparing with the normal group, contents of IL-1β, IL-6 and TNF-α in the serum of the model group significantly increased (P<0.01). Comparing with the model group, each test sample has effect of reducing contents of IL-1β, IL-6 and TNF-α in the serum at certain degree, wherein the cartilage extract+CURCUMAE LONGAE RHIZOMA extract group, cartilage extract+CURCUMAE LONGAE RHIZOMA extract+ cators of synovial fluid: comparing with the normal group, content of MMP-3 in the synovial fluid of the swelling tissue of the model groups significantly increased (P<0.01). Comparing with the model group, each test sample has effect of reducing content of MMP-3 in the tissue at certain degree, wherein the formula group showed the most significant effect (P<0.05). Comparing with the normal group, content of COL-II in the synovial fluid of the swelling tissue of the model group significantly decreased (P<0.01). Comparing with the model group, each test sample has effect of increasing content of COL-II in the synovial fluid at certain degree, but the difference is not significant (P>0.05). Results are shown in Table 7.

TABLE 5

Effects of the composition on biochemical indicators in serum of Freund's adjuvant-induced arthritis model rats (Mean ± SD)

| Group | IL-1β (pg/mL) | IL-6 (pg/mL) | TNF-α (pg/mL) |
|---|---|---|---|
| A. normal group | 113.42 ± 25.97** | 787.25 ± 120.12** | 78.35 ± 10.39** |
| B. model group | 509.61 ± 16.47 | 1579.92 ± 71.57 | 253.40 ± 19.00 |
| C. cartilage extract group | 487.01 ± 60.36 | 1471.27 ± 166.23 | 235.47 ± 36.05 |
| D. CURCUMAE LONGAE RHIZOMA extract group | 441.68 ± 76.07 | 1417.31 ± 132.32 | 218.08 ± 40.74 |
| E. COICIS SEMEN extract group | 472.17 ± 62.03 | 1531.38 ± 152.87 | 231.85 ± 32.36 |
| F. cartilage extract + CURCUMAE LONGAE RHIZOMA extract group | 422.82 ± 82.72* | 1404.23 ± 162.10* | 217.24 ± 31.33* |
| G. cartilage extract + CURCUMAE LONGAE RHIZOMA extract + COICIS SEMEN extract group | 410.20 ± 83.09* | 1374.56 ± 147.16* | 209.11 ± 27.76** |
| H. formula group (Example 2) | 387.14 ± 83.28** | 1232.20 ± 157.22** | 191.03 ± 32.30** |

TABLE 6

Effects of the composition on biochemical indicators of swelling foot tissue of Freund's adjuvant-induced arthritis model rats (Mean ± SD)

| Group | PGE2 (pg/mg) | IL-1β (pg/mg) |
|---|---|---|
| A. normal group | 199.94 ± 23.66** | 311.00 ± 88.03** |
| B. model group | 429.96 ± 39.00 | 686.49 ± 79.44 |
| C. cartilage extract group | 412.73 ± 30.86 | 619.06 ± 89.78 |
| D. CURCUMAE LONGAE RHIZOMA extract group | 391.80 ± 31.18 | 608.43 ± 77.55 |
| E. COICIS SEMEN group | 397.58 ± 43.74 | 652.18 ± 75.30 |
| F. Cartilage extract + CURCUMAE LONGAE RHIZOMA extract group | 384.29 ± 40.37 | 608.90 ± 89.27 |
| G. Cartilage extract + CURCUMAE LONGAE RHIZOMA extract + COICIS SEMEN extract group | 381.80 ± 34.49* | 593.43 ± 66.62 |
| H. formula group (Example 2) | 364.07 ± 61.21** | 572.85 ± 93.98* |

TABLE 7

Effects of the composition on MMP-3, COL-II in synovial fluid of Freund's adjuvant-induced arthritis model rats (Mean ± SD)

| Group | MMP-3 (pg/mL) | COL-II (pg/mL) |
|---|---|---|
| A. normal group | 91.92 ± 20.91** | 371.70 ± 46.45** |
| B. model group | 244.11 ± 32.26 | 199.45 ± 36.25 |
| C. cartilage extract group | 228.43 ± 38.93 | 216.62 ± 47.77 |
| D. CURCUMAE LONGAE RHIZOMA extract group | 216.16 ± 32.47 | 231.31 ± 59.35 |
| E. COICIS SEMEN extract group | 223.80 ± 46.51 | 222.56 ± 34.22 |
| F. cartilage extract + CURCUMAE LONGAE RHIZOMA extract group | 213.36 ± 45.26 | 236.89 ± 52.20 |
| G. cartilage extract + CURCUMAE LONGAE RHIZOMA extract + COICIS SEMEN extract group | 200.46 ± 42.33 | 237.04 ± 74.52 |
| H. formula group (Example 2) | 192.83 ± 30.52* | 245.93 ± 39.54 |

Comment: comparing with the model group,
*P < 0.05; and
**P < 0.01

5.5 Measure of Articular Cavity

Comparing with the normal group, the articular cavity area of ankle joint of the model group significantly increased (P<0.01). Comparing with the model group, each test sample has effect of reducing articular cavity area of the ankle joint at certain degrees, where in the effect of the formula group was the most significant (P<0.05). Results are shown in Table 8.

TABLE 8

Effects of the composition on articular cavity area of ankle of Freund's 2 adjuvant-induced arthritis model rats (mm$^2$, Mean ± SD)

| Group | articular cavity (mm$^2$) |
|---|---|
| A. normal group | 20.76 ± 3.10** |
| B. model group | 40.32 ± 4.17 |
| C. cartilage extract group | 37.32 ± 9.57 |
| D. CURCUMAE LONGAE RHIZOMA group | 35.43 ± 5.33 |
| E. COICIS SEMEN group | 37.73 ± 8.90 |
| F. Cartilage extract + CURCUMAE LONGAE RHIZOMA group | 34.36 ± 5.83 |
| G. Cartilage extract + CURCUMAE LONGAE RHIZOMA + COICIS SEMEN group | 33.21 ± 7.27 |
| H. formula group (Example 2) | 31.15 ± 5.67* |

Comment: comparing with the model group,
*P < 0.05; and
**P < 0.01.

Thus, the composition of the present disclosure has functions of reducing arthrocele degree, decreasing arthritis index, ameliorating physiological index of arthritis and reducing articular cavity area, and can be used for manufacturing health care foods or foods for reducing arthrocele degree, decreasing arthritis index, ameliorating physiological index of arthritis and reducing articular cavity area.

The above descriptions are only preferred embodiments of the present disclosure. It should be noted that a number of modifications and refinements may be made by one or ordinary skill in the art without departing from the principles of the disclosure, and such modifications and refinements are also considered to be within the scope of protection of the disclosure.

What is claimed is:

1. A medicine composition with a function of protecting joints, comprising parts by weight: 5 to 10 parts of *Curcumae longae* rhizome extract, 25 to 35 parts of cartilage extract, 5 to 15 parts of *Coicis semen* extract and 0.1 to 0.5 parts of *Puerariae lobatae* radix extract.

2. The medicine composition according to claim 1, comprising parts by weight: 10 parts of *Curcumae longae* rhizome extract, 35 parts of cartilage extract, 15 parts of *Coicis semen* extract, and 0.5 parts of *Puerariae lobatae* radix extract.

3. The medicine composition according to claim 1, which is in a form of a health care food.

4. The medicine composition according to claim 3, wherein dosage form of the health care food is oral liquid, capsule, tablet, powder, effervescent, granule or tableted candy.

5. The medicine composition according to claim 3, wherein the health care food further comprises a food additive.

6. A method of producing the medicine composition according to claim 1, comprising mixing parts by weight: 5 to 10 parts of *Curcumae longae* rhizome extract, 25 to 35 parts of cartilage extract, 5 to 15 parts of *Coicis semen* extract and 0.1 to 0.5 parts of *Puerariae lobatae* radix extract.

7. A method of relieving arthritis, comprising administering an effective amount of the composition according to claim 1 to a subject in need thereof.

8. The method according to claim 7, wherein the relieving arthritis is one or more selected from reducing arthrocele degree, decreasing arthritis index, ameliorating biochemical index of arthritis and reducing articular cavity area.

* * * * *